(12) United States Patent
Yang et al.

(10) Patent No.: US 11,786,530 B2
(45) Date of Patent: Oct. 17, 2023

(54) METHOD AGAINST SEVERE ACUTE RESPIRATORY SYNDROME CORONAVIRUS 2 INFECTION

(71) Applicant: National Yang Ming Chiao Tung University, Hsinchu (TW)

(72) Inventors: Jinn-Moon Yang, Hsinchu (TW); Po-Shiuan Hsieh, Taipei (TW); Chih-Heng Huang, Hsinchu (TW); Yu-Hsiu Chang, Taipei (TW); Nikhil Pathak, Hsinchu (TW); Yen-Chao Hsu, Hsinchu (TW); Yun-Ti Chen, Tainan (TW); Nung-Yu Hsu, Hsinchu (TW)

(73) Assignee: NATIONAL YANG MING CHIAO TUNG UNIVERSITY, Hsinchu (TW)

( * ) Notice: Subject to any disclaimer, the term of this patent is extended or adjusted under 35 U.S.C. 154(b) by 0 days.

(21) Appl. No.: 17/690,321

(22) Filed: Mar. 9, 2022

(65) Prior Publication Data
US 2022/0288080 A1    Sep. 15, 2022

Related U.S. Application Data

(60) Provisional application No. 63/160,507, filed on Mar. 12, 2021.

(51) Int. Cl.
| | | |
|---|---|---|
| *A61K 31/519* | (2006.01) | |
| *A61P 31/14* | (2006.01) | |
| *A61K 31/675* | (2006.01) | |
| *A61K 31/402* | (2006.01) | |
| *A61K 45/06* | (2006.01) | |

(52) U.S. Cl.
CPC .......... *A61K 31/519* (2013.01); *A61K 31/402* (2013.01); *A61K 31/675* (2013.01); *A61K 45/06* (2013.01); *A61P 31/14* (2018.01)

(58) Field of Classification Search
CPC .... A61K 31/519; A61K 31/675; A61K 45/06; A61K 31/706; A61K 31/402; A61K 31/53; A61K 2300/00; A61P 31/14
See application file for complete search history.

(56) References Cited

PUBLICATIONS

Caruso A, Caccuri F, Bugatti A, Zani A, Vanoni M, Bonfanti P, Cazzaniga ME, Perno CF, Messa C, Alberghina L. Methotrexate inhibits SARS-CoV-2 virus replication "in vitro". J Med Virol. Mar. 2021;93(3):1780-1785. doi: 10.1002/jmv.26512. Epub Sep. 28, 2020. PMID: 32926453; PMCID: PMC7891346. (Year: 2020).*

Wang, M., Cao, R., Zhang, L. et al. Remdesivir and chloroquine effectively inhibit the recently emerged novel coronavirus (2019-nCoV) in vitro. Cell Res 30, 269-271 (2020). (Year: 2020).*

Arnaldo Caruso et al., "Methotrexate inhibits SARS-CoV-2 virus replication 'in vitro.'" Journal of Medical Virology, 93(3), pp. 1780-1785, 2020.

Kim M. Stegmann et al., "The folate antagonist methotrexate diminishes replication of the coronavirus SARS-CoV-2 and enhances the antiviral efficacy of remdesivir in cell culture models," Virus Research, 302 (198469), pp. 1-14, 2021.

* cited by examiner

*Primary Examiner* — Theodore R. Howell
(74) *Attorney, Agent, or Firm* — Hamre, Schumann, Mueller & Larson, P.C.

(57) ABSTRACT

Disclosed herein is a method against severe acute respiratory syndrome coronavirus 2 (SARS-CoV-2) infection. The method includes administering to a subject in need thereof a first active ingredient selected from the group consisting of methotrexate (MIX) and a pharmaceutically acceptable salt thereof, and a second active ingredient selected from the group consisting of remdesivir and a pharmaceutically acceptable salt thereof. A molar ratio of the first active ingredient to the second active ingredient ranges from 1:13 to 1:25.

6 Claims, No Drawings

METHOD AGAINST SEVERE ACUTE RESPIRATORY SYNDROME CORONAVIRUS 2 INFECTION

CROSS-REFERENCE TO RELATED APPLICATION

This application claims priority of U.S. Provisional Application No. 63/160,507, filed on Mar. 12, 2021.

FIELD

The present disclosure relates to a method against severe acute respiratory syndrome coronavirus 2 (SARS-CoV-2) infection using methotrexate (MTX) and remdesivir.

BACKGROUND

Severe acute respiratory syndrome coronavirus 2 (SARS-CoV-2) is an enveloped, positive-sense, single-stranded RNA betacoronavirus that causes a pandemic of acute respiratory disease, denoted as coronavirus disease 2019 (COVID-19). Major symptoms of COVID-19 include respiratory symptoms such as fever above 38° C., cough, shortness of breath, difficulty in breathing, severe pneumonia, and acute respiratory distress syndrome (ARDS). Symptoms such as loss of smell and taste, diarrhea, headache, chills, loss of appetite, general malaise, and impaired consciousness may be observed.

Combination therapy, such as use of an anti-inflammation drug (e.g., dexamethasone and anti-interleukin-6 monoclonal antibody) and an antiviral drug (e.g., remdesivir), is the primary treatment strategy for combating COVID-19.

Methotrexate (MIX) is a multi-target inhibitor of dihydrofolate reductase (DHFR), thymidylate synthase (TYMS) and AICAR (5-aminoimidazole-4-carboxamide ribonucleotide) formyltransferase/IMP (inosine monophosphate) cyclohydrolase (RTIC), and has been approved for treatment of rheumatoid arthritis (RA) and cancer. It has been reported that, MIX can exert a dose-dependent, potent inhibition of SARS-CoV-2 replication in model cell lines, and can be used as a first-line intervention even against heavily mutated SARS-CoV-2 variants or emerging epidemics caused by novel RNA viruses (Caruso A. et al. (2021), *J Med Virol.*, 93:1780-1785).

In spite of the aforesaid, there is still a need to develop a new strategy that is effective against SARS-CoV-2.

SUMMARY

Therefore, an object of the present disclosure is to provide a method against severe acute respiratory syndrome coronavirus 2 (SARS-CoV-2) infection, which can alleviate at least one of the drawbacks of the prior art.

The method includes administering to a subject in need thereof a first active ingredient selected from the group consisting of methotrexate (MIX) and a pharmaceutically acceptable salt thereof, and a second active ingredient selected from the group consisting of remdesivir and a pharmaceutically acceptable salt thereof. A molar ratio of the first active ingredient to the second active ingredient ranges from 1:13 to 1:25.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

The present disclosure provides a method against severe acute respiratory syndrome coronavirus 2 (SARS-CoV-2) infection, which includes administering to a subject in need thereof a first active ingredient selected from the group consisting of methotrexate (MIX) and a pharmaceutically acceptable salt thereof, and a second active ingredient selected from the group consisting of remdesivir and a pharmaceutically acceptable salt thereof. A molar ratio of the first active ingredient to the second active ingredient ranges from 1:13 to 1:25.

As used herein, the term "against SARS-CoV-2 infection" or "anti-SARS-CoV-2 infection" means prevention of infection by SARS-CoV-2, suppression of SARS-CoV-2 replication, and/or treatment and/or prevention of infectious diseases caused by SARS-CoV-2.

As used herein, the term "administration" or "administering" means introducing, providing or delivering a pre-determined active ingredient to a subject by any suitable routes to perform its intended function.

As used herein, the term "subject" refers to any animal of interest, such as humans, monkeys, hamsters, cows, sheep, horses, pigs, goats, dogs, cats, mice, and rats. In certain embodiments, the subject is a human.

As used herein, the term "pharmaceutically acceptable salt" refers to any salt, which, upon administration to the subject, is capable of providing (directly or indirectly) a compound as described herein (i.e., MIX and remdesivir) without undue toxicity, irritation, allergic response and the like. In particular, "pharmaceutically acceptable salt" may encompass those approved by a regulatory agency of the federal or a state government or listed in the U.S. Pharmacopeia or other generally recognized pharmacopeia for use in animals, and more particularly in humans. The preparation of salts can be carried out by methods known in the art.

For instance, the pharmaceutically acceptable salts of MIX and remdesivir may be acid addition salts, base addition salts or metallic salts, and they can be synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture thereof. Examples of the acid addition salts may include mineral acid addition salts such as, for example, hydrochloride, hydrobromide, hydroiodide, sulfate, nitrate, and phosphate; and organic acid addition salts such as, for example, acetate, maleate, fumarate, citrate, oxalate, succinate, tartrate, malate, mandelate, methanesulphonate, p-toluenesulphonate, 2-naphtalenesulphonate, and 1,2-ethanedisulphonate. Examples of the base addition salts may include inorganic salts such as, for example, ammonium; and organic alkali salts such as, for example, ethylenediamine, ethanolamine, N,N-dialkylenethanolamine, triethanolamine, choline, glucamine, and basic amino acids salts. Examples of the metallic salts may include, for example, sodium, potassium, calcium, magnesium, aluminium, and lithium salts.

In certain embodiments, the molar ratio of the first active ingredient to the second active ingredient ranges from 1:13 to 1:20. In an exemplary embodiment, the molar ratio of the first active ingredient to the second active ingredient ranges from 1:13 to 1:15.

In certain embodiments, the first and second active ingredients may be administered as two separate dosage forms, each containing one of the active ingredients. The two separate dosage forms may be administered substantially concurrently, or may be administered alternately or sequentially on the same day. That is, the first and second active ingredients may be administered simultaneously or sequentially.

According to the present disclosure, each of the first and second active ingredients may be prepared into a pharmaceutical composition in a dosage form suitable for, e.g., parenteral or oral administration, using technology well known to those skilled in the art.

According to the present disclosure, the suitable dosage form for oral administration includes, but is not limited to, sterile powders, tablets, troches, lozenges, pellets, capsules, dispersible powders or granules, solutions, suspensions, emulsions, syrup, elixir, slurry, and the like.

The pharmaceutical composition according to the present disclosure may be administered via one of the following parenteral routes: intraperitoneal injection, intrapleural injection, intramuscular injection, intravenous injection, intraarterial injection, intraarticular injection, intrasynovial injection, intrathecal injection, intracranial injection, intraepidermal injection, subcutaneous injection, intradermal injection, intralesional injection, and sublingual administration.

According to the present disclosure, the pharmaceutical composition may further include a pharmaceutically acceptable carrier widely employed in the art of drug-manufacturing. For instance, the pharmaceutically acceptable carrier may include one or more of the following agents: solvents, buffers, emulsifiers, suspending agents, decomposers, disintegrating agents, dispersing agents, binding agents, excipients, stabilizing agents, chelating agents, diluents, gelling agents, preservatives, fillers, wetting agents, lubricants, absorption delaying agents, liposomes, and the like. The choice and amount of the aforesaid agents are within the expertise and routine skills of those skilled in the art.

The dose and frequency of administration of the pharmaceutical composition of the present disclosure may vary depending on the following factors: the severity of the illness or disorder to be treated, routes of administration, and age, physical condition and response of the subject to be treated. In general, the probiotic composition may be administered in a single dose or in several doses.

The disclosure will be further described by way of the following examples. However, it should be understood that the following examples are solely intended for the purpose of illustration and should not be construed as limiting the disclosure in practice.

EXAMPLES

General Experimental Materials:
1. Source and Cultivation of Vero E6 Cells

African green monkey kidney (Vero E6) cells (ATCC® CRL-1586) were purchased from American Type Culture Collection (ATCC, Manassas, Va., USA). The Vero E6 cells were grown in a 10-cm Petri dish containing Dulbecco's Modified Eagle's Medium (DMEM) (Cat. No. SH30243.01, HyClone) supplemented with 10% fetal bovine serum (FBS) (Cat. No. SH30396.03, HyClone) and 1% antibiotic-antimycotic (Cat. No. 15240-062, Gibco), which is referred to as "E1 medium" hereinafter. The Vero E6 cells were cultivated in an incubator with culture conditions set at 37° C. and 5% $CO_2$. Medium change was performed every two to three days. Cell passage was performed when the cultured cells reached 803-90% of confluence.

2. Severe Acute Respiratory Syndrome Coronavirus 2 (SARS-CoV-2) Solution

The SARS-CoV-2 WA strain used in the following experiments was provided by the Chang Gung Medical Foundation, the Linkou Chang Gung Memorial Hospital (Taiwan). The SARS-CoV-2 WA strain was dissolved in DMEM (Cat. No. SH30243.01, HyClone) supplemented with 2% FBS (Cat. No. SH30396.03, HyClone), which is referred to as "E2 medium" hereinafter, so as to prepare a SARS-CoV-2 solution having a virus amount of 500 pfu/mL. The SARS-CoV-2 solution was stored in a freezer at −80° C. for further experiment.

3. Treating agents
(1) Methotrexate (MTX) Solution

The methotrexate solution used in the following experiments contained 0-0.5 M methotrexate dihydrate (Cat. No. AS-10155, Key Organics).

(2) Remdesivir Solution

The remdesivir solution used in the following experiments contained 0-5 M remdesivir (Cat. No. HY-104077, MedChemExpress).

Example 1

Evaluation for the Effect of the Combination of Methotrexate (MTX) and Remdesivir Against SARS-CoV-2

Experimental Procedures:

Vero E6 cells were divided into 10 groups, including one normal control group, one pathological control group, two comparative groups (i.e., comparative groups 1 to 2), and six experimental groups (i.e., experimental groups 1 to 6). Each group of the Vero E6 cells was incubated in a respective well of a 96-well culture plate containing 100 μL of E1 medium at $1\times10^4$ cells/well, followed by cultivation in an incubator (37° C., 5% $CO_2$) for 24 hours. Afterwards, the culture medium in each well was removed, and the Vero E6 cells of a respective one of the two comparative groups and six experimental groups were added with 100 μL of the SARS-CoV-2 solution prepared in section 2 of the General Experimental Materials, so that the Vero E6 cells were infected with SARS-CoV-2 at a median tissue culture infectious doses (TCIDO of 10, and were treated with a suitable amount of the methotrexate solution and/or the remdesivir solition prepared in section 3 of the General Experimental Materials.

In addition, the Vero E6 cells of the normal control group were added with 100 μL of E2 medium, and were not added with the SARS-CoV-2 solution and any treating agent. The Vero E6 cells of the pathological control group were added with 100 μL of the SARS-CoV-2 solution prepared in section 2 of the General Experimental Materials, and were not added with any treating agent.

The treating agent(s) and the final concentration thereof for each group are summarized in Table 1 below.

TABLE 1

| Group | Treating agent | | Molar ratio of MTX to remdesivir |
|---|---|---|---|
| | MTX (μM) | Remdesivir (μM) | |
| Normal control group | — | — | — |
| Pathological control group | — | — | — |
| Comparative group 1 | 0 | 3 | — |
| Comparative group 2 | 0.2 | 0 | — |
| Experimental group 1 | 0.3 | 1 | 1:3.3 |
| Experimental group 2 | 0.2 | 2 | 1:10 |
| Experimental group 3 | 0.3 | 4 | 1:13.3 |
| Experimental group 4 | 0.2 | 3 | 1:15 |
| Experimental group 5 | 0.2 | 4 | 1:20 |
| Experimental group 6 | 0.2 | 5 | 1:25 |

Each group was cultivated in an incubator (37° C., 5% $CO_2$) for 3 days. The liquid in each well was removed, followed by adding 50 μL of 3-[4,5-dimethylthiazol-2-yl]-2,5-diphenyltetrazoli-um bromide (MTT). After cultivation in an incubator (37° C., 5% $CO_2$) for 4 hours, the liquid in each well was removed, and 100 μL of dimethyl sulfoxide (DMSO) was added into the respective well to dissolve formazan dye, followed by subjecting the mixture thus obtained to determination of absorbance at a wavelength of 590 nm ($OD_{590}$) by an EMax® precision microplate reader (Molecular Devices, USA).

The inhibition rate PO was calculated using the following Equation (I):

$$A=(B-D)/(C-D)-100 \quad (I)$$

where A=inhibition rate (%)
B=$OD_{590}$ value of the respective experimental group, the respective comparative group, or the pathological control group
C=$OD_{590}$ value of the normal control group
D=$OD_{590}$ value of the pathological control group In addition, the delta synergy score of each group was calculated based on zero interaction potency (ZIP) model, thereby analyzing the drug interaction relationships by comparing the change in the potency of the dose-response curves between individual drugs (i.e., MTX and remdesivir) and their combinations.

Results:

Table 2 shows the inhibition rate and the delta synergy score in each group. It can be seen from Table 2 that the inhibition rates determined in the experimental groups 3 to 6, were each higher than those determined in the experimental group 2, the comparative groups 1 to 2, the normal control group, and the pathological control group.

In addition, based on the delta synergy score results, it can be demonstrated that the excellent inhibition rate of the experimental groups 3 to 6 was due to the synergistic interaction between MTX and remdesivir. Furthermore, when the molar ratio of MTX to remdesivir in decimal form was larger than or equal to 1/10 (the decimal form of the molar ratio 1:10), it had been observed that the delta synergy score was unsatisfactory and even might be negative, showing a suboptimal inhibition. Particularly, when 0.3 μM of MTX and 1 μM of remdesivir were used in the experimental group 1 (i.e., the molar ratio of 1:3.3 was applied), the delta synergy score was −10.89.

TABLE 2

| Group | Inhibition rate (%) | Delta synergy score |
|---|---|---|
| Normal control group | — | — |
| Pathological control group | 0 | — |
| Comparative group 1 | 4.57 | — |
| Comparative group 2 | 11.71 | — |
| Experimental group 1 | 51.22 | −10.89 |
| Experimental group 2 | 20.43 | 8.97184 |
| Experimental group 3 | 82.5 | 9.52 |
| Experimental group 4 | 87.85 | 55.6681 |
| Experimental group 5 | 55.57 | 44.17959 |
| Experimental group 6 | 49.36 | 43.41403 |

Summarizing the above test results, it is clear that MTX and remdesivir, when used in combination in a specified molar ratio, can act synergistically against SARS-CoV-2 infection.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method against severe acute respiratory syndrome coronavirus 2 (SARS-CoV-2) infection, comprising administering to a subject in need thereof a first active ingredient selected from the group consisting of methotrexate (MTX) and a pharmaceutically acceptable salt thereof, and a second active ingredient selected from the group consisting of remdesivir and a pharmaceutically acceptable salt thereof,
   wherein a molar ratio of the first active ingredient to the second active ingredient is 1:15.
2. The method according to claim 1, wherein the first and second active ingredients are administered simultaneously.
3. The method according to claim 1, wherein the first and second active ingredients are administered sequentially.
4. The method according to claim 1, wherein at least one of the first and second active ingredients is in a dosage form for oral administration.
5. The method according to claim 1, wherein at least one of the first and second active ingredients is in a dosage form for parenteral administration.
6. The method according to claim 1, wherein the first active ingredient is included at 0.2 μM and the second active ingredient is included at 3 μM.

* * * * *